US008725668B2

(12) United States Patent
Georgopoulos

(10) Patent No.: US 8,725,668 B2
(45) Date of Patent: May 13, 2014

(54) CLASSIFYING AN ITEM TO ONE OF A PLURALITY OF GROUPS

(75) Inventor: Apostolos Georgopoulos, Minneapolis, MN (US)

(73) Assignees: Regents of the University of Minnesota, St. Paul, MN (US); U.S. Department of Veterans Affairs, Washington, DC (US)

( * ) Notice: Subject to any disclaimer, the term of this patent is extended or adjusted under 35 U.S.C. 154(b) by 286 days.

(21) Appl. No.: 13/259,580

(22) PCT Filed: Mar. 24, 2010

(86) PCT No.: PCT/US2010/028504
§ 371 (c)(1),
(2), (4) Date: Sep. 23, 2011

(87) PCT Pub. No.: WO2010/111392
PCT Pub. Date: Sep. 30, 2010

(65) Prior Publication Data
US 2012/0023050 A1     Jan. 26, 2012

Related U.S. Application Data

(60) Provisional application No. 61/162,921, filed on Mar. 24, 2009.

(51) Int. Cl.
*G06F 15/18* (2006.01)
(52) U.S. Cl.
USPC .......................................................... 706/20
(58) Field of Classification Search
None
See application file for complete search history.

(56) References Cited

U.S. PATENT DOCUMENTS

| 6,129,665 | A | 10/2000 | Zanin | |
| 8,306,942 | B2 * | 11/2012 | Chen et al. | 706/62 |
| 2005/0124863 | A1 | 6/2005 | Cook | |
| 2005/0170528 | A1 | 8/2005 | West et al. | |
| 2005/0209785 | A1 * | 9/2005 | Wells et al. | 702/19 |
| 2007/0269804 | A1 | 11/2007 | Liew et al. | |
| 2008/0091118 | A1 | 4/2008 | Georgopoulos | |
| 2008/0103996 | A1 | 5/2008 | Forman et al. | |
| 2008/0133141 | A1 | 6/2008 | Frost | |
| 2008/0228677 | A1 | 9/2008 | Kenedy et al. | |
| 2009/0318773 | A1 * | 12/2009 | Jung et al. | 600/300 |
| 2011/0270348 | A1 | 11/2011 | Goetz | |

OTHER PUBLICATIONS

Dudoit, Fridlyand, Speed, "Comparison of Discrimination Methods for the Classification of Tumors Using Gene Expression Data", Technical Report #576, Department of Statistics, University of California, Berkeley, Jun. 2000, pp. 1-43.*
Schapire, Freund, Bartlett, Lee, "Boosting the Margin: A New Explanation for the Effectiveness of Voting Methods", The Annals of Statistics, vol. 26, No. 5, Oct. 1998, pp. 1651-1686.*

(Continued)

*Primary Examiner* — Kakali Chaki
*Assistant Examiner* — Walter Hanchak
(74) *Attorney, Agent, or Firm* — Dicke, Billig & Czaja, PLLC

(57) ABSTRACT

A method of classifying an item to one of a plurality of groups includes providing a plurality of predictors associated with the item. For each predictor, the item is assigned to one of the groups. An assignment number is determined for each group. The item is classified to one of the groups based on the assignment number for each group.

19 Claims, 3 Drawing Sheets

(56) References Cited

OTHER PUBLICATIONS

Yan, Zheng, "Discriminant Analysis Using Multigene Expression Profiles in Classification of Breast Cancer", International Conference on Bioinformatics & Computational Biology, BIOCOMP 2007, vol. II, Jun. 25-28, 2007, Las Vegas Nevada, USA. 2007, pp. 643-649.*

Selinger et al., "Measuring Synchronization in Neuronal Networks for Biosensor Applications", Biosensors and Bioelectronics, vol. 19, Issue 7, Feb. 15, 2004, pp. 675-683.

Non-Final Office Action for U.S. Appl. No. 13/312,332 mailed Mar. 20, 2013, 12 pgs.

Georgopoulos, Apostolos P., et al., Synchronous neural interactions assessed by magnetoencephalography: a functional biomarker for brain disorders, Journal of Neural Engineering, 2007, pp. 349-355, 4, IOP Publishing Ltd., UK.

Georgopoulos, Apostolos P., et al., The Synchronous neural interactions test as a functional neuromarker for post-traumatic stress disorder (PTSD): a robust classification method based on the bootstrap, Journal of Neural Engineering, 2010, pp. 1-7, IOP Publishing Ltd., UK.

"Dynamic nonlinear modeling of neural ensemble activity", Program of BMSR Workshop at the EMBC 2011, Aug. 30, 2011, 2 pgs.

PCT Search Report mailed May 7, 2010, 8 pgs.

* cited by examiner

US 8,725,668 B2

CLASSIFYING AN ITEM TO ONE OF A PLURALITY OF GROUPS

CROSS-REFERENCE TO RELATED APPLICATIONS

This application is a U.S. national stage application claiming priority under 35 U.S.C. §371 to International Application Serial No. PCT/US10/28504, filed Mar. 24, 2010, which claims priority under 35 U.S.C. §119(e)(1) to U.S. Provisional Patent Application Ser. No. 61/162,921, filed Mar. 24, 2009, entitled "Classifying an Item to One of a Plurality of Groups", and the entire teachings of which are incorporated herein by reference.

BACKGROUND

Classification of an item (e.g., a person or subject) to one or another group (e.g., healthy or disease) is a common problem. When measurements of several variables ("predictors") are available as measurements per item, classical discriminant methods can be used to address this problem. These methods were initiated by Fisher in 1936 and have been extended in different variants since then. Typically, these methods involve: (1) the analysis of a training set of items from which classification functions are derived; (2) these functions are then applied to predictor measurements of a new item, yielding a classification score for each group; and (3) the new item is classified to the group with the highest score. Conventional classification techniques include: Linear discriminant classification analysis, which uses predictor measurements; quadratic discriminant classification analysis (QDA), which uses predictor measurements and their squares and products; Bayesian classifiers, which use adaptable, prior information; and support vector machines, which use non-linear parcellation of predictor space.

There are several limitations of these conventional classification methods. First, these methods may be useful for a relatively small number of predictors (e.g., in the tens), but the methods can become intractable for large predictor sets. A large number of predictors may often be available, but all of the available predictors are not typically used by the conventional methods. In addition, as the number of predictors increases, and if, somehow, all of them can be used, the result is commonly "overfitting", which means an excellent classification rate of the groups in the training set but a poor classification of new subjects (i.e., poor "external cross-validation"). Another problem is that from a large predictor set, only a small subset might be most useful, and other predictors may simply add noise. So, even if, technically, all of the predictors could be used, this does not necessarily mean that they would improve the classification outcome.

SUMMARY

One embodiment provides a method of classifying an item to one of a plurality of groups. The method includes providing a plurality of predictors associated with the item. For each predictor, the item is assigned to one of the groups. An assignment number is determined for each group. The item is classified to one of the groups based on the assignment number for each group.

Another embodiment provides a system for automatically classifying an item to one of a plurality of groups. The system includes a measurement device configured to generate a plurality of predictors associated with the item, and a controller configured to perform, for each predictor, an assignment of the item to one of the groups based on predictor distributions for known classified items, and classify the item to one of the groups based on a number of the assignments for each group.

Yet another embodiment provides a system for automatically classifying an item to one of a plurality of groups. The system includes a measurement device configured to generate a plurality of predictors associated with the item, and a controller configured to perform, for each predictor, an assignment of the item to one of the groups, determine an assignment number for each group, and classify the item to one of the groups based on the assignment number for each group.

DETAILED DESCRIPTION

One embodiment provides a system and method for performing direct classification in a large predictor space. When a large number of predictors are available (e.g. thousands or more), classification becomes problematic because standard discriminant analyses typically cannot be used due to the fact that the number of items providing the predictors is typically much smaller (e.g. tens or hundreds) than the number of predictors. One embodiment of a classification method set forth herein does not use discriminant classification functions. Instead, for each predictor, the method according to one embodiment assigns the item to be classified to one or the other of two groups (in the case of two-group classification) using statistics (e.g., confidence intervals on the group distributions), and then counts the number of assignments to each of the two groups. The winner (i.e., the group to which the particular item is classified) according to one embodiment is the group with the most assignments across the whole predictor space.

One embodiment provides a system for automatically classifying an item to one of a plurality of groups. A plurality of predictors associated with the item is provided to the system. For each predictor, an assignment of the item to one of the groups is performed by the system based on predictor distributions for known classified items. The system classifies the item to one of the groups based on the number of the assignments for each group.

Figure 1:
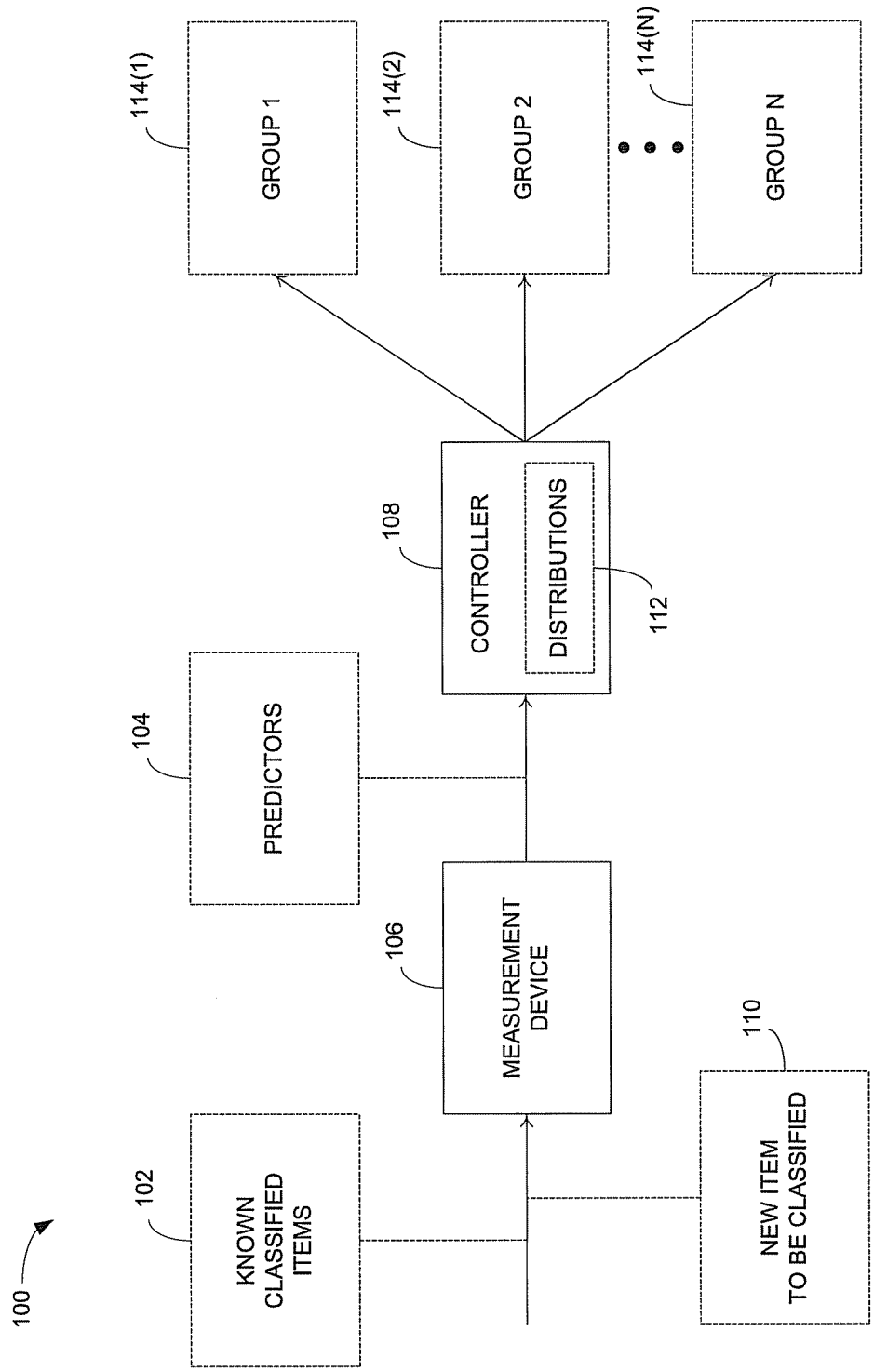
FIG. 1 is a block diagram illustrating a system for automatically classifying an item to one of a plurality of groups according to one embodiment.

FIG. 1 is a block diagram illustrating a system 100 for automatically classifying an item to one of a plurality of groups according to one embodiment. As shown in FIG. 1, a plurality of known classified items 102 are provided to a measurement device 106. Measurement device 106 performs a plurality of measurements on each of the known classified items 102, and generates a plurality of predictors 104 for each of the known classified items 102. The predictors 104 are provided to controller 108, which generates a plurality of predictor distributions 112. After the predictor distributions 112 have been generated for the known classified items 102, a new item 110 with an unknown classification is provided to the measurement device 106. Measurement device 106 performs a plurality of measurements on the new item 110, and generates a plurality of predictors 104 for the new item 110.

The predictors 104 for the new item 110 are provided to controller 108, which automatically classifies new item 110 to one of a plurality of groups 114(1)-114(N) (collectively referred to as groups 114) based on the received predictors 104 for the new item 110 and the predictor distributions 112.

In one embodiment, system 100 is configured to perform classification based on biomagnetism data. Biomagnetism refers to the measurement of magnetic fields from sources within the body. These fields are produced by magnetic materials or ionic currents associated with biological activity. One application in the field of biomagnetism involves the measurement of human brain activity, such as with a magnetoencephalography (MEG) device. A MEG device measures magnetic fields produced by electrical activity in the brain.

In one embodiment, items 102 and 110 represent human subjects (e.g., patients) and measurement device 106 is a MEG device configured to perform synchronous MEG interactions tests using 248 sensors, such as "SQUIDS". A SQUID (Superconducting Quantum Interference Device) is a superconducting device for detecting magnetic fields. A SQUID, along with its associated feedback electronics, provides an output voltage proportional to the magnetic flux applied to its detection coil.

In one embodiment, the device 106 includes a helmet configured for "whole head" analysis of a subject and includes more than 100 sensors or SQUID channels. As mentioned above, in one embodiment, 248 sensors or channels are used. When a group of neurons (for example, 10,000 or more), are activated together, the magnetic field produced by the net current may be detected by the coils of the SQUIDS in device 106.

The classification analysis according to one embodiment begins with a plurality of subjects with known classifications (i.e., known classified items 102), with each subject being classified to one of a number, N, of different groups 114, where "N" is an integer greater than one. In one embodiment, the number, N, of groups 114 is equal to two, and system 100 is configured to perform two-group classification. In one form of this embodiment, the two groups are disease (e.g., Multiple Sclerosis (MS), Alzheimer's disease (AD), etc.) and healthy. In another embodiment, the number, N, is greater than two and system 100 is configured to perform multiple-group classification. In one embodiment, device 106 performs measurement of dynamic synchronous neural interactions (SNI) among neuronal populations which correspond to brain function, and based on the measured data (i.e., predictors 104), controller 108 provides accurate, differential classification from among one or more of the following conditions: a normal condition, Alzheimer's Disease, pre-dementia syndrome, mild cognitive impairment, schizophrenia, Sjögren's Syndrome, alcoholism, alcohol impairment, fetal alcohol syndrome, multiple sclerosis, Parkinson's Disease, bipolar disorder, traumatic brain injury, depression, autoimmune disorder, a neurodegenerative disorder, pain, or a disease affecting the central nervous system.

In one embodiment, predictors 104 include 30,628 predictors for each item (e.g., human subject) 102 and 110, which are the zero-lag, partial cross correlations, $PC^0$, between all possible pairs of the 248 sensors of device 106. The zero-lag, partial cross correlations provide estimates of the strength and sign (positive, negative) of direct synchronous coupling between neuronal populations at, for example, a 1 millisecond (ms) temporal resolution.

In one embodiment, controller 108 comprises a computing system or computing device that includes at least one processor and memory. Depending on the exact configuration and type of computing device, the memory may be volatile (such as RAM), non-volatile (such as ROM, flash memory, etc.), or some combination of the two. The memory used by controller 108 is an example of computer storage media. Computer storage media used by controller 108 according to one embodiment includes volatile and nonvolatile, removable and non-removable media implemented in any suitable method or technology for storage of information such as computer readable instructions, data structures, program modules or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium that can be used to store the desired information and that can be accessed by controller 108.

Figure 2:
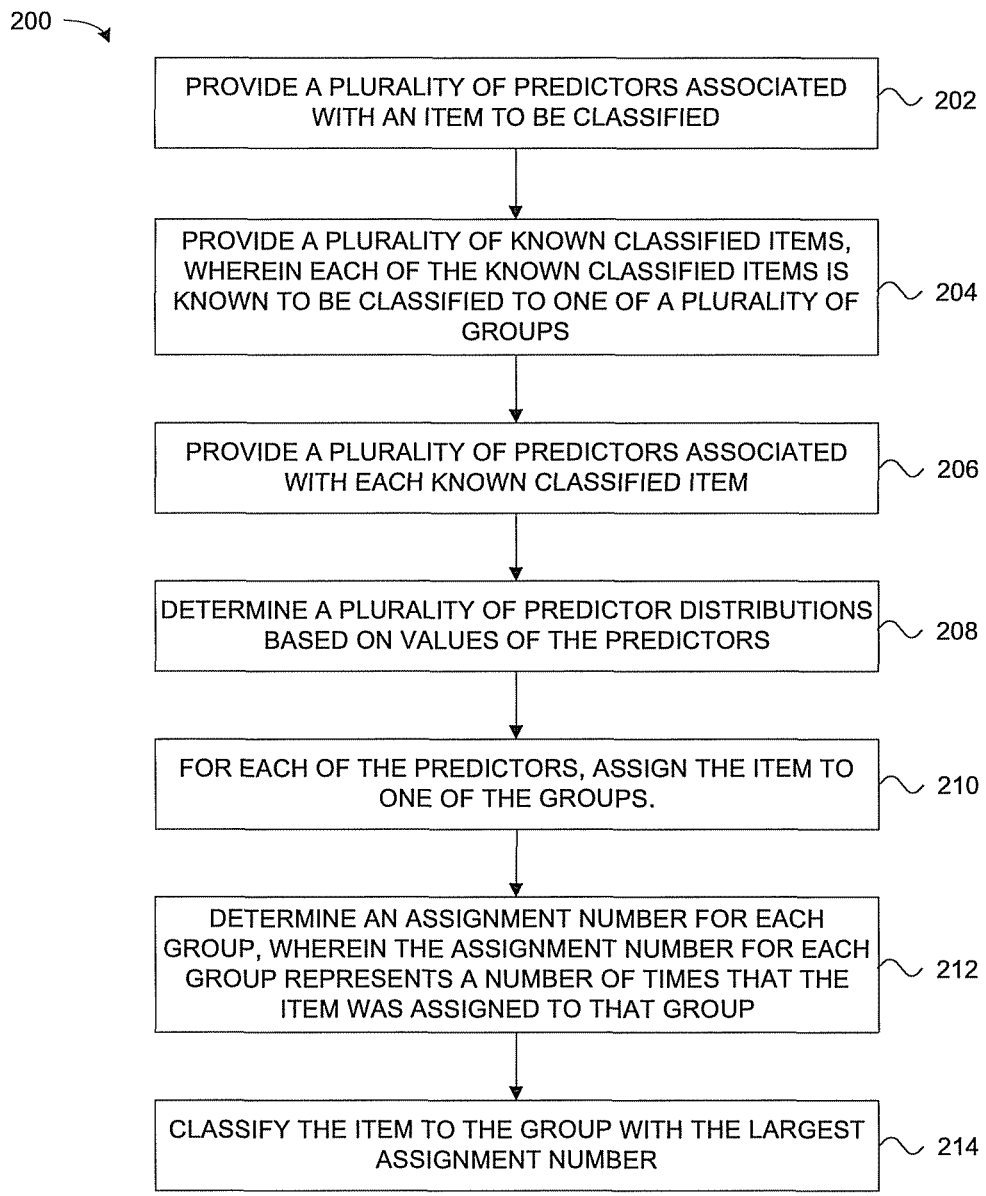
FIG. 2 is a flow diagram illustrating a method of automatically classifying an item to one of a plurality of groups according to one embodiment.

FIG. 2 is a flow diagram illustrating a method 200 of automatically classifying an item 110 to one of a plurality of groups 114 according to one embodiment. In one embodiment, system 100 (FIG. 1) is configured to perform method 200. At 202 in method 200, a plurality of predictors 104 associated with the item 110 to be classified is provided. At 204, a plurality of known classified items 102, wherein each of the known classified items is known to be classified to one of the groups 114, is provided. At 206, a plurality of predictors 104 associated with each known classified item 102 is provided. At 208, a plurality of predictor distributions 112 is determined based on values of the predictors 104. In one embodiment, the plurality of predictor distributions 112 determined at 208 includes N distributions for each of the predictors 104, wherein N represents the number of groups 114 in the plurality of groups. At 210, for each of the predictors 104, the item 110 is assigned to one of the groups 114. In one embodiment, the assigning of the item 110 to one of the groups 114 for each predictor 104 at 210 is performed based on the plurality of distributions 112 determined at 208 using a one-sample t-test as described in further detail below. At 212, an assignment number is determined for each group 114, wherein the assignment number for each group 114 represents a number of times that the item 110 was assigned to that group 114. At 214, the item 110 is classified to the group 114 with the largest assignment number.

In one embodiment of method 200, the number of predictors 104 associated with each known classified item 102 is substantially larger than the number of known classified items 102. In one embodiment, the number of predictors 104 for each item 102 exceeds the number of items 102 by at least a factor of 100. In one form of method 200, the predictors 104 represent biomagnetism data generated with a MEG device; the item 110 to be classified is a human subject; and the groups 114 include a disease group and a healthy group. In other embodiments, other types of predictors 104, items 102 and 110, and groups 114 may be used to perform any desired type of classification.

As mentioned above with respect to FIG. 2, the assigning of the item 110 to one of the groups 114 for each predictor 104 at 210 in method 200 is performed in one embodiment based on the plurality of distributions 112 determined at 208 using a one-sample t-test. Assume for example that the known classified items 102 include two groups 114 of subjects, one healthy (H) group and another group with a disease (D). Also assume that the numbers of subjects in H and D are $N_H$ and $N_D$, respectively, and each subject has 30,628 predictors 104 (e.g., $PC^0$ predictors, z-transformed for analysis), which are generated by measurement device 106. Conversely, for each predictor m (m=1 to 30,628), there are two distributions 112 available: $N_H^m$ and $N_D^m$. In one embodiment, the number of distributions in distributions 112 equals the number of groups 114 times the number of predictors 104 for each item 102. Thus, for two-group classification and 30,628 predictors for each item 102, distributions 112 will include 61,256 different distributions (i.e., one distribution for each of the 30,628 predictors for the healthy group H, and one distribution for each of the 30,628 predictors for the disease group D. If these distributions were illustrated with a graph, the horizontal axis would represent predictor values, and the vertical axis would represent number of people.

Assume further for the above example that the new item 110 to be classified is a human subject S that comes in to be classified with predictors m=30,628 $PC^O$ ($S_m$). In one embodiment, controller 108 is configured to classify the new subject in the following manner: (1) For each predictor m, assign $S_m$ to the H or D group 114; (2) count the number of times $S_m$ was assigned to H ($n_H$) and to D ($n_D$) groups; and (3) the subject S is classified to the group 114 with the larger number of assignments.

In one embodiment, the assignment of $S_m$ to the H or D group 114 for each predictor value, m, is performed using a one-sample t-test (P<0.05, two-tailed), which tests the null hypothesis that $S_m$ is equal to the mean of the H or D group 114. During the t-test, a standard formula is used to calculate a t-score based on the predictor values, the mean value of the H or D distributions, and a standard error value. A P-value is determined (e.g., using a standard table of t-scores) based on the calculated t-score. In one embodiment, if the P-value is less than 0.05, the null hypothesis is rejected. Thus, depending on the result of the one-sample t-test, the null hypothesis (that $S_m$ is equal to the mean of the H or D group) may (if P<0.05) or may not be rejected (if P≥0.05). There are 4 possible outcomes for each m comparison: (1) The null hypothesis is rejected for H but not for D ($S_m \rightarrow H$, add 1 to $n_H$); (2) the null hypothesis is rejected for D but not for H ($S_m \rightarrow D$, add 1 to $n_D$); (3) the null hypothesis is rejected for both H and D ($S_m$ cannot be assigned; outlier); (4) the null hypothesis cannot be rejected for either H or D ($S_m$ cannot be assigned; full overlap).

In one embodiment, to make the tests for H and D as comparable as possible, the constraint is placed that the variances of the $N_H^m$ and $N_D^m$ distributions tested against $S_m$ may not differ significantly (Fisher's test, P<0.05, one-tailed). Potential options include changing the probability levels and using non-parametric statistics. In one embodiment, weighting is used for each predictor based on the amount of overlap of the distributions for the predictor. For example, in one embodiment, predictors with distributions that have a relatively large overlap are weighted less than predictors with distributions having little or no overlap. The weighting results in a weighted sum that is determined in the second step mentioned above (i.e., counting the number of times $S_m$ was assigned to H ($n_H$) and to D ($n_D$) groups), with the weighted sum determining the classification of the subject. In other embodiments, other weighting techniques may be used.

The performance of the classification method used by system 100 has been assessed in an external cross-validation context. Using the specifics above and applying the classification method on the absolute value of the z-transformed $PC^O$, 89.05% correct classification was obtained (80.5% specificity and 97.6% sensitivity) for a sample with 41 MS patients and 41 matched healthy subjects, and 95.6% correct classification was obtained (91.2% specificity and 100% sensitivity) for a sample with 34 AD patients and 34 matched healthy subjects. The results can be further improved in some cases by employing non-parametric measures for group assignment. For example, using such a criterion based on median and weighted interquartile difference, 100% correct specificity and sensitivity has been obtained for the MS sample mentioned above. However, non-parametric approaches are in general more variable and are typically tailored to specific distributions.

The classification method used by system 100 has also been applied to post-traumatic stress disorder (PTSD) patients in a bootstrap-based approach. The details and results of the test are described in A. P. Georgopoulos et al., "The synchronous neural interactions test as a functional neuromarker for post-traumatic stress disorder (PTSD): a robust classification method based on bootstrap", Journal of Neural Engineering 7 (Jan. 20, 2010) 016011, available at stackslop.org/JNE/7/016011, which is hereby incorporated by reference herein. The test involved a PTSD group with 74 patients with confirmed PTSD as their primary diagnosis, and a control group with 250 healthy subjects within the age range of the PTSD patients. Applying the classification method on the absolute value of the z-transformed $PC^O$ predictors, 92.4% correct classification was obtained (87.6% specificity and 97.3% sensitivity).

Figure 3:
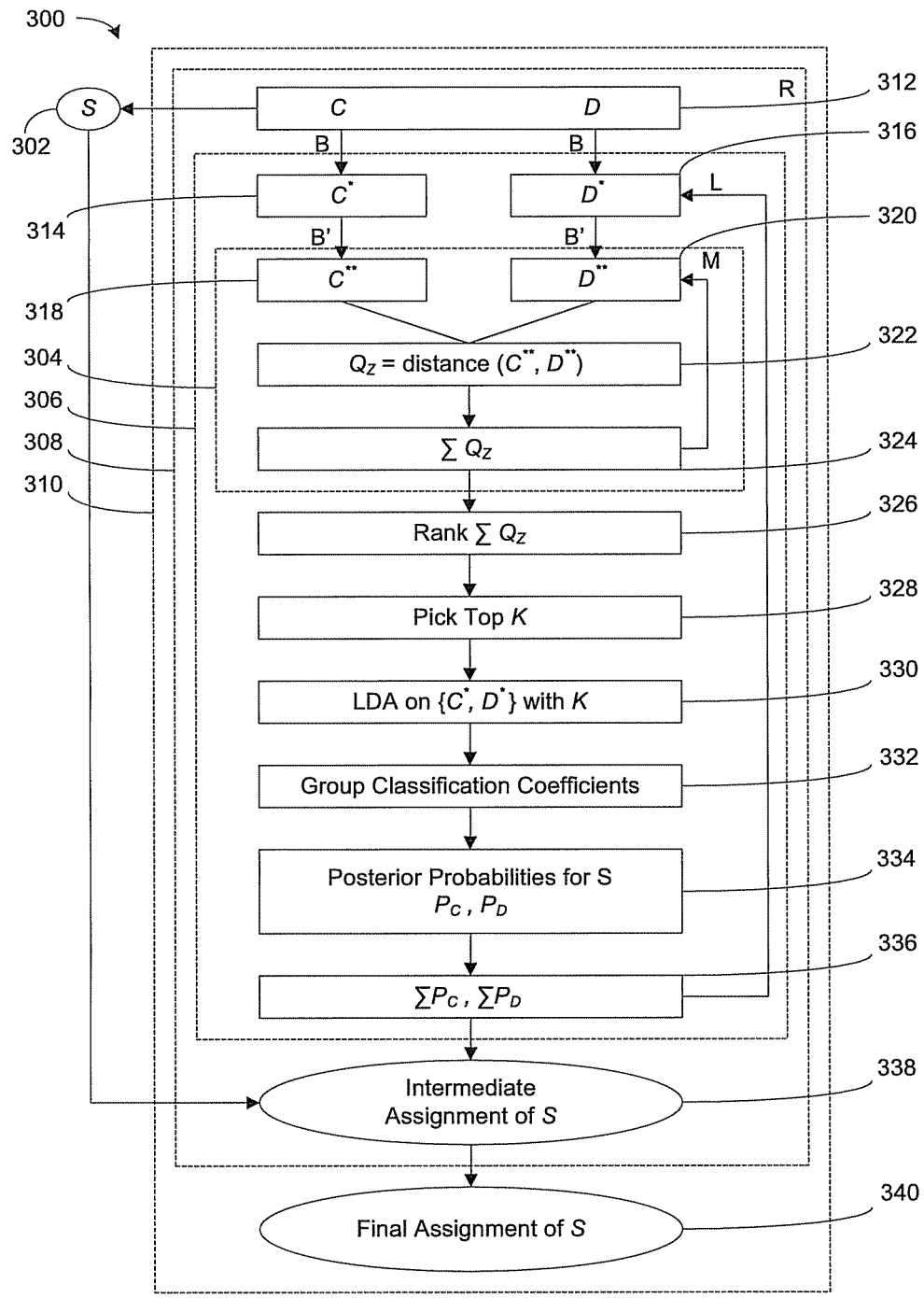
FIG. 3 is a flow diagram illustrating a method of automatically classifying an item to one of a plurality of groups according to another embodiment.

FIG. 3 is a flow diagram illustrating a method 300 of automatically classifying an item 110 to one of a plurality of groups 114 according to another embodiment. In one embodiment, system 100 (FIG. 1) is configured to perform method 300. Method 300 was used in the classification of PTSD patients mentioned above. As shown in FIG. 3, three distinct bootstrap loops 304, 306, and 308 are integrated into the classification procedure. The classification of each new subject 302 (S), randomly selected from the total sample of both control (C) and disease (D) groups ($N_{TOTAL}=N_C+N_D=250+74=324$), is the first step (Step 1 described below) and begins at 312, within loop 308. Thereafter, two equal-size bootstrap samples ($B=N_{C*}=N_{D*}$) are composed from the remaining pool of subjects ($N_C+N_D-1$) and this (Step 2 described below) is indicated in FIG. 3 as the parallel arrows stemming from block 312 in loop 308 into loop 306 towards the two bootstrapped samples. From C* and D* at 314 and 316, respectively, another two new sets of equal-size bootstrap samples are composed ($B'=B=N_{C}=N_{D}$) as the classification procedure enters loop 304 and blocks 318 and 320. Within loop 304, at 322, a measure of distance Q between the two groups for a given predictor (Z) of the two groups is determined and summed cumulatively at 324 over M repetitions (Step 3 described below). This cumulative sum of the distance measure ($\Sigma Q_Z$) is ranked at 326 for all 30,628 predictors, and the top-ranking K predictors (picked at 328) are used at 330 and 332 to derive group classification coefficients using Linear Discriminant Analysis (LDA) on C* and D*.

Next, the posterior probabilities for the assignment of S into either the control or diseased group are calculated at 334 and cumulatively summed over L repetitions at 336. Loop 306 represents the series of calculations (Steps 4, 5, 6 described below) for each of the L repetitions, each of which also includes loop 304 of M repetitions. From these cumulative posterior probabilities ($\Sigma p_C$ and $\Sigma p_D$), the external subject S is classified based on the larger cumulative probability of the two. This intermediate assignment process (Steps 2 through 6 described below) is repeated R times. This is represented by loop 308, which encompasses both loops 304 and 306. Finally, the outer loop 310 represents the full classification procedure, which is described in further detail below.

Classification of individual subjects to the PTSD or control group using method 300 involves a bootstrap approach. The bootstrap approach was motivated by the common practical situation where a "new" subject S needs to be classified, given subjects of known condition, i.e. belonging to a control (i.e. non-PTSD) group C or to the PTSD group D. In classical discriminant analyses, S is assigned to the group (C or D) which yields the greater classification score in a single run. However, a major objective in clinical practice is to evaluate, if possible, S's assignment with respect to the larger populations C' and D', of which C and D are samples. Classification rates for C' and D' can be approximated using the bootstrap, by calculating S's assignment R times with respect to bootstrap samples of equal (between groups) and sufficiently large size B drawn with replacement from C and D. In this way, R assignments (i.e. classification outcomes and corresponding posterior probabilities) are obtained from which S's classification is then computed (based on the outcomes of R bootstraps), together with a confidence interval on the assignment. A sufficiently large number G of subjects (per group) can thus be classified to obtain long-term estimates of the accuracy of classification. This approach provides a more realistic and practically more useful evaluation of S's assignment than a single run, since it takes into account the variability of C and D.

At 312 in method 300, C and D denote the control and disease (PTSD) samples, respectively, where $N_C=250$ and $N_D=74$ subjects ($N_{TOTAL}=N_C+N_D=324$ subjects). The analysis proceeded in the following steps.

Step 1: Subject to be Classified.

The "external" subject 302 (S) to be classified is left out of the calculations in steps 2-5 below.

Step 2: First-Stage Bootstrap Samples for Classification Coefficients.

From the remaining subjects, two bootstrap samples C* and D* of equal size $B=N_{C*}=N_{D*}$ are composed at 314 and 316 by resampling with replacement from C and D, respectively. These samples will be used to generate classification coefficients for an intermediate classification of S. This step is shown in FIG. 3 as the parallel arrows from loop 308 leading into loop 306, wherein the two bootstrap samples are composed.

Step 3: Second-Stage Bootstrap Samples for Predictor Selection Based on a Distance Measure.

Two new bootstrap samples, C and D of equal size $B'=N_{C}=N_{D}$ are composed at 318 and 320 by resampling with replacement from C* and D*, respectively. Next, for each Z predictor, a distance measure $Q_Z$ between C and D is calculated at 322 based on some attribute ξ of $z_{ij}^0$ (e.g. mean, median, variance, etc.) and keep a running sum of $Q_Z$, $\Sigma Q_Z$, over a number of M repetitions of this step, as indicated at 324. This is illustrated in FIG. 3 as the procedures within loop 304, which culminates in the cumulative sum of the distance measure between the two samples' predictors ($z_{ij}^0$).

Step 4: Predictor Selection.

Rank-order $\Sigma Q_Z$ is performed at 326, and the K number of Z predictors with the top-ranked $\Sigma Q_Z$ are picked and retained at 328. These are the predictors with the highest potential for separating the two groups. (Notice that this procedure does not rely on, and is independent of, any classification analysis.)

Step 5: Classification Coefficients from First-Stage Bootstrap Samples.

At 330 and 332 in method 300, the K predictors are used to derive classification functions for the two groups (i.e. control and PTSD) using the C* and D* samples as input subjects in a linear discriminant analysis (LDA).

Step 6: Intermediate Classification of S (Includes Steps 6.1-6.4).

Step 6.1.

The functions determined in step 5 are used at 334 in method 300 to compute pairs of posterior probabilities $p_C^S$ and $p_D^S$ that S belongs to the control or disease group, respectively.

Step 6.2.

As indicated at 336, method 300 keeps running sums of $\Sigma p_C^S$ and $\Sigma p_D^S$ over a number of L repetitions of steps 2 through 5. (These calculations are shown in FIG. 3, as the analysis moves from loop 304 to continue within loop 306 where the posterior probabilities are cumulatively summed over the L repetitions.)

Step 6.3. Intermediate Classification:

At 338 in method 300, at the end of L repetitions, subject S is classified based on the greater sum: If $\Sigma p_C^S > \Sigma p_D^S$, subject S is assigned to the control C group, whereas if $\Sigma p_C^S < \Sigma p_D^S$, subject S is assigned to the disease D (PTSD) group. (If $\Sigma p_C^S = \Sigma p_D^S$, the analysis is repeated). This step is depicted in FIG. 3 as the analysis moves from loop 306 into loop 308. Very similar results are obtained if the binary outcomes of the intermediate classification are used instead of the posterior probabilities, although the posterior probabilities may be preferred due to their finer grain.

Step 6.4.

Repeat steps 1 through 6.3 R times to generate a large sample of intermediate classifications. This is illustrated as the procedures within loop 308, which encompasses loops 304 and 306.

Step 7: Systematic Evaluation of Classification Parameters.

For any number of R intermediate classifications, compute the measures given in the following Equations I-III:

$$\text{Sensitivity}(\%) = \frac{\text{Number of patients correctly classified}}{\text{Total number of patients}} \times 100 \quad \text{Equation I}$$

$$\text{Specificity}(\%) = \frac{\text{Number of control subjects correctly classified}}{\text{Total number of control subjects}} \times 100 \quad \text{Equation II}$$

$$\text{Overall accuracy}(\%) = \frac{\text{Sensitivity} + \text{Specificity}}{2} \quad \text{Equation III}$$

The measures given in Equations I-III allow for a quick way (for small L and R) to assess key parameters employed, namely, the sizes of bootstrap samples (B,B'), the number of predictors (K), the number of bootstrap iterations (M, L, R), and the ξ attribute of $z_{ij}^0$. This is represented by loop 310 in FIG. 3.

At 340 in method 300, a final classification or assignment of the external subject S is performed, including confidence intervals. The description above outlined the bootstrap-based classification procedure and provided the means by which to assess the performance of the classifier for different parameter values based on intermediate classifications of S. The following description presents a procedure by which the external subject is ultimately classified and by which confidence intervals are generated on the classification outcome. Let $r_C^S$ and $r_D^S$ be the running counts of intermediate S assignments to group C or D, respectively, over a suitably large number of R repetitions of steps 2-6. Then, the resulting proportions of classification to each one of the two groups, $$h_C^S = \frac{r_C^S}{R} \text{ and } h_D^S = \frac{r_D^S}{R},$$

can be regarded as long-term, expected probabilities for classifying S to the control or the PTSD group, respectively, at a 0.5 probability threshold (for a binary outcome). Corresponding confidence intervals are obtained by bootstrapping $h_C^S$ and $h_D^S$ over a W number of R. Then, $h_C^S$ and $h_D^S$ (and their confidence intervals) denote the strength (and associated uncertainty) of single subject classification, based on the existing C and D samples.

The classification method used by system 100 according to one embodiment does not involve training sets, can be executed fast, is superior to simple correlation measures, provides robust results with respect to the sample size of H and D distributions, and has wide applicability, beyond MEG data. The classification method according to one embodiment works piecemeal, and does not use large memory to store huge variance-covariance matrices (used in classical discriminant analyses). In one embodiment, system 100 is configured to utilize all useful information in the predictors 104 (i.e., instead of using only a subset of the information), and perform external cross-validation of the outcome. In one embodiment, system 100 is configured to use the absolute values of z-transformed $PC^0$ rather than signed values. It has been determined that the information for classification lies in the strength of the relation between sensor series, and less in the sign of the slope of the relation.

Although the present disclosure has been described with reference to preferred embodiments, workers skilled in the art will recognize that changes can be made in form and detail without departing from the spirit and scope of the present disclosure.

What is claimed is:

1. A method of classifying an item to one of a plurality of groups, comprising: providing a plurality of predictors associated with the item; for each predictor, assigning the item to one of the groups based on predictor distributions for known classified items; determining an assignment number for each group, wherein the assignment number for each group represents a number of times that the item was assigned to that group based on the plurality of predictors; and classifying the item to one of the groups based on the assignment number for each group.

2. The method of claim 1, wherein classifying the item to one of the groups based on the assignment number for each group comprises:
classifying the item to the group with a largest assignment number.

3. The method of claim 1, and further comprising: providing a plurality of known classified items, wherein each of the known classified items is known to be classified to one of the groups; providing a plurality of predictors associated with each known classified item; and determining the predictor distributions for the known classified items based on values of the predictors.

4. The method of claim 3, wherein the assigning of the item to one of the groups for each predictor is performed using a one-sample t-test.

5. The method of claim 3, wherein the plurality of predictor distributions include N distributions for each of the predictors, wherein N represents a number of the groups in the plurality of groups.

6. The method of claim 3, wherein a number of the predictors associated with each known classified item is substantially larger than a number of the known classified items.

7. The method of claim 6, wherein the number of predictors exceeds the number of known classified items by at least a factor of 100.

8. The method of claim 1, wherein the predictors represent biomagnetism data, and wherein the item is a human subject.

9. The method of claim 8, wherein the biomagnetism data is generated with a magnetoencephalography (MEG) device.

10. The method of claim 1, wherein the assigning, determining, and classifying are performed by at least one processor.

11. A system for automatically classifying an item to one of a plurality of groups, comprising:
a measurement device configured to generate a plurality of predictors associated with the item; and
a controller configured to perform, for each predictor, an assignment of the item to one of the groups based on predictor distributions for known classified items, and classify the item to one of the groups based on a number of the assignments for each group.

12. The system of claim 11, wherein the controller is configured to classify the item to the group with a largest number of the assignments.

13. The system of claim 11, wherein the measurement device is configured to generate a set of predictors for each of the known classified items, and wherein the predictor distributions for the known classified items are determined based on values of the predictors for the known classified items, and wherein the predictor distributions are weighted.

14. The system of claim 13, wherein the controller is configured to perform, for each predictor, the assignment of the item to one of the groups based on the predictor distributions for the known classified items using a one-sample t-test.

15. The system of claim 14, wherein a number of the predictors for each known classified item exceeds a number of the known classified items by at least a factor of 100.

16. The system of claim 11, wherein the predictor distributions include N distributions for each of the predictors, wherein N represents a number of the groups in the plurality of groups.

17. The system of claim 11, wherein the predictors represent biomagnetism data, and wherein the item is a human subject.

18. The system of claim 17, wherein the measurement device comprises a magnetoencephalography (MEG) device.

19. A system for automatically classifying an item to one of a plurality of groups, comprising: a measurement device configured to generate a plurality of predictors associated with the item; and a controller configured to perform, for each predictor, an assignment of the item to one of the groups based on predictor distributions for known classified items, determine an assignment number for each group, and classify the item to one of the groups based on the assignment number for each group, wherein the assignment number for each group represents a number of times that the item was assigned to that group based on the plurality of predictors.

* * * * *